US00PP37697P2

(12) United States Plant Patent
Wyckstandt

(10) Patent No.: US PP37,697 P2
(45) Date of Patent: Sep. 15, 2026

(54) ***AGAPANTHUS* PLANT NAMED 'A21001'**

(50) Latin Name: *Agapanthus hybrid*
Varietal Denomination: A21001

(71) Applicant: Tim Wyckstandt, Aalter (BE)

(72) Inventor: Tim Wyckstandt, Aalter (BE)

(73) Assignee: VAN VLIET NEW PLANTS B.V., Stroe (NL)

( * ) Notice: Subject to any disclaimer, the term of this patent is extended or adjusted under 35 U.S.C. 154(b) by 0 days.

(21) Appl. No.: 19/422,443

(22) Filed: Dec. 17, 2025

(30) Foreign Application Priority Data

Aug. 19, 2025 (QZ) ..... PBR 20251673

(51) Int. Cl.
*A01H 5/02* (2018.01)
*A01H 6/04* (2018.01)

(52) U.S. Cl.
USPC ..... Plt./398

(58) Field of Classification Search
USPC ..... Plt./398
See application file for complete search history.

(56) References Cited

U.S. PATENT DOCUMENTS

PP35,644 P2 * 2/2024 Bean ..... Plt./398

* cited by examiner

*Primary Examiner* — Susan McCormick Ewoldt
*Assistant Examiner* — Zachariah Allan Kay
(74) *Attorney, Agent, or Firm* — Penny J. Aguirre

(57) ABSTRACT

A new cultivar of *Agapanthus* plant named 'A21001' that is characterized by its floriferous and re-blooming habit with a long flowering period, its flowers that are large in size, its deep blue colored flowers with blue filaments, and its tall plant height.

3 Drawing Sheets

Botanical classification: *Agapanthus* hybrid.
Varietal denomination: 'A21001'.

CROSS REFERENCE TO RELATED APPLICATIONS

This application claims priority to European Community Plant Variety Office (CPVO) Plant Breeder's Rights Application No. 2025/1673, filed Aug. 19, 2025. The Applicant received the information for the Plant breeders' rights application directly from the Inventor. This application is co-pending with a U.S. Plant Patent Applications filed for a plant patent derived from the same breeding program that is entitled *Agapanthus* Plant Named 'A19002' (U.S. Plant patent application Ser. No. 19/422,442), *Agapanthus* Plant Named 'A22004' (U.S. Plant patent application Ser. No. 19/422,445), *Agapanthus* Plant Named 'Su Casa' (U.S. Plant patent application Ser. No. 19/422,434), and *Agapanthus* Plant Named 'Vitro002' (U.S. Plant patent application Ser. No. 19/422,451).

BACKGROUND OF THE INVENTION

The present invention relates to a new and distinct cultivar of *Agapanthus* of hybrid origin and will be referred to hereafter by its cultivar name, 'A21001'. 'A21001' represents a new perennial grown for landscape and container use.

'A21001' was discovered in July of 2021 as a single unique plant by the Inventor from amongst seedlings in a trial field in Aalter, Belgium. The trial field had been planted with numerous unpatented and unnamed proprietary plants from the Inventor's breeding program. The parents are therefore unknown.

Asexual propagation of the new cultivar was first accomplished by division by the Inventor in Aalter, Belgium in August of 2023. Asexual propagation by division and tissue culture utilizing meristematic tissue has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'A21001' as a distinct cultivar of *Agapanthus*.

1. 'A21001' exhibits a floriferous and re-blooming habit with a long flowering period.
2. 'A21001' exhibits large size flowers.
3. 'A21001' exhibits deep blue colored flowers with blue filaments.
4. 'A21001' exhibits a tall plant height (reaching an average of 80 cm).

'A21001' can be most closely compared to the *Agapanthus* cultivars Andbin (U.S. Plant Pat. No. 26,336 and 'DWAGHYB01' (U.S. Plant Pat. No. 35,644). 'Andbin' is similar to 'A21001' in having blue flowers and repeat blooming. 'Andbin' differs from 'A21001' in having a much shorter plant height and less intensely colored blue flowers. 'DWAGHYB01' is similar to 'A21001' in having blue flowers and a tall plant height. 'DWAGHYB01' differs from 'A21001' in having foliage that is bent more downward, a less floriferous blooming habit, and a shorter blooming period.

'A21001' can also be compared to the co-pending cultivars of *Agapanthus*; 'A19002', 'A22004', 'Su Casa' and 'Vitro002'. 'A19002' differs from 'A21001' in having white flowers. 'A22004' differs from 'A21001' in having violet-blue flowers with a darker central stripe on the tepals. 'Su Casa' differs from 'A21001' in having light violet-blue flowers. 'Vitro002' differs from 'A21001' in having white flowers with yellow filaments.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the effective filing date.

BRIEF DESCRIPTION OF THE DRAWINGS

The accompanying color photographs illustrate the overall appearance and distinct characteristics of the new *Agapanthus*. The photographs were taken of plants 19 months in age of 'A21001' as grown in an unheated poly-covered tunnel in a 19-cm container in Aalter, Belgium.

The photograph in FIG. 1 provides a side view of a plant of 'A21001' in bloom.

Figure 1:
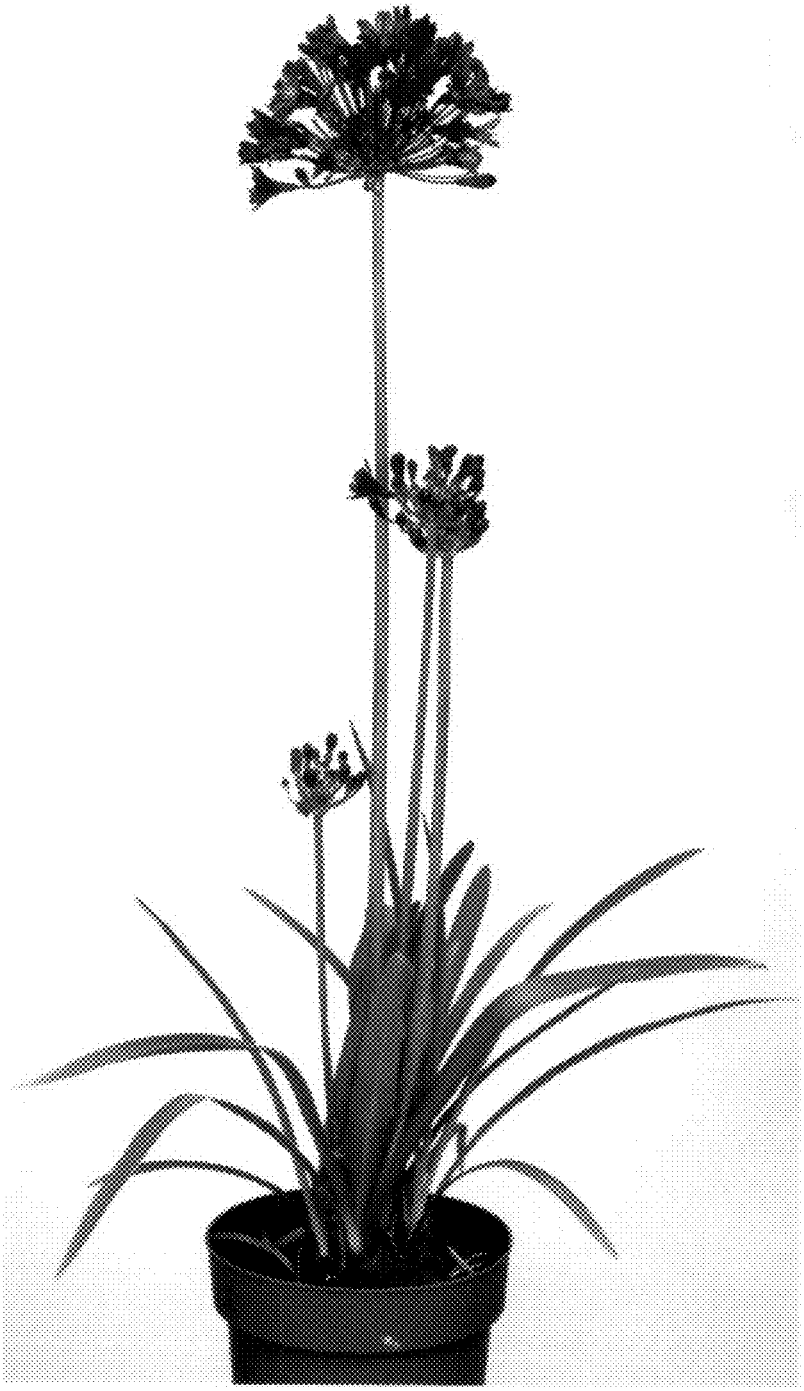
Figure 2:
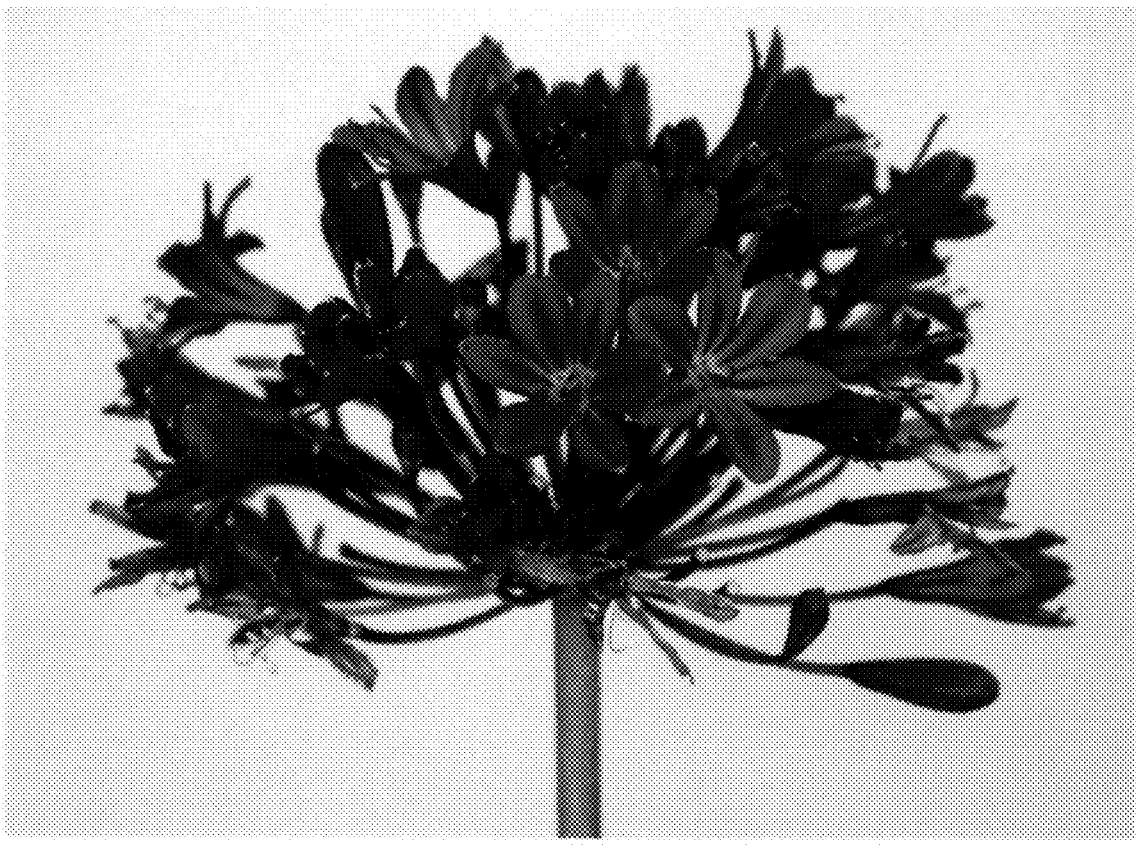

The photograph in FIG. 2 provides a close-up view of an inflorescence of 'A21001'.

Figure 3:
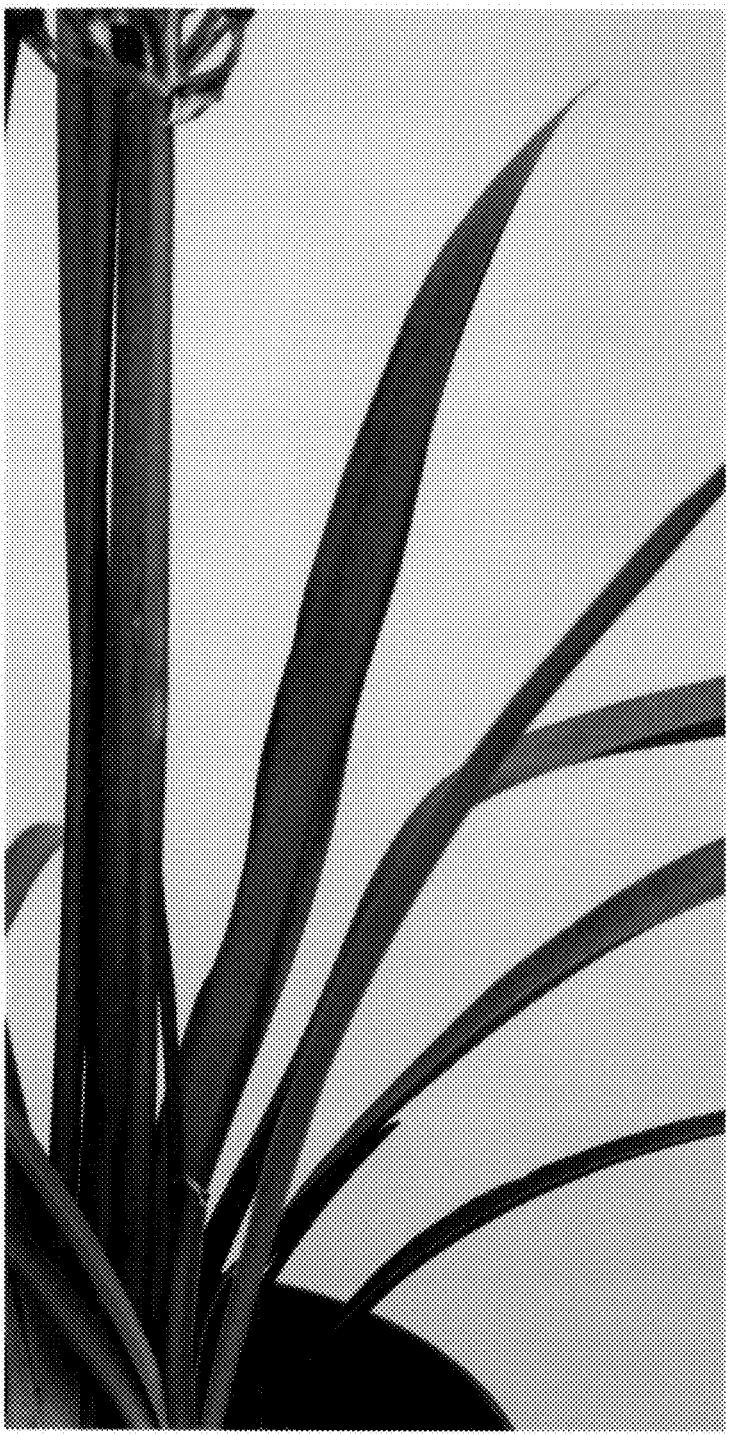

The photograph in FIG. 3 provides a close-up view of the foliage of 'A21001'.

The colors in the photographs are as close as possible with the photographic and printing technology utilized and color values cited in the detailed botanical description accurately describe the colors of the new *Agapanthus*.

DETAILED BOTANICAL DESCRIPTION

The following is a detailed description of 19-month-old plants of 'A21001' as grown in an unheated poly-covered tunnel in 19-cm containers in Aalter, Belgium. The phenotype of the new cultivar may vary with variations in environmental, climatic, and cultural conditions, as it has not been tested under all possible environmental conditions. The color determinations are in accordance with The 2015 (2019 reprint) Colour Chart of The Royal Horticultural Society, London, England, except where general color terms of ordinary dictionary significance are used.

General description:

- *Blooming period.*—End of May into November in Belgium.
- *Plant type.*—Semi-deciduous (climate dependent) herbaceous perennial.
- *Plant habit.*—Basal rosettes with inflorescences emerging from the rosette center.
- *Height and spread.*—80 cm in height and 50 cm in spread as grown in the landscape.
- *Hardiness.*—At least in U.S.D.A. Zones 8 to 12.
- *Diseases and pests.*—No resistance or susceptibility to diseases or pests has been observed.
- *Root description.*—Thick and fleshy.
- *Propagation.*—Division and tissue culture.

Foliage description:

- *Leaf shape.*—Ligulate.
- *Leaf division.*—Simple.
- *Leaf base.*—Decurrent, broadly cuneate.
- *Leaf apex.*—Acute.
- *Leaf aspect.*—Moderately carinate, slightly to moderately curved.
- *Leaf venation.*—Parallel, upper surface; 144B, lower surface; 137B, secondary veins 137B.
- *Leaf margins.*—Entire.
- *Leaf size.*—Up to 26.6 cm in length and up to 1.9 cm in width.
- *Leaf surface.*—Both surfaces non-rugose, upper surface slightly glossy, lower surface very slightly glossy.
- *Leaf number.*—Average of 6 leaves per rosette.
- *Foliage density.*—Medium.
- *Leaf color.*—Young leaves upper surface; 143A, young leaves lower surface; a blend of 138A and 143A, mature leaves upper surface; NN137B, mature leaves lower surface; 137B.
- *Leaf attachment.*—Sessile to base.

Flower description:

- *Inflorescence type.*—Umbel, hemispherical.
- *Flower fragrance.*—None.
- *Flower type.*—Rotate, campanulate, base of tepals fused.
- *Flower number.*—An average of 10 flowers per umbel, 160 buds and flowers per plant.
- *Inflorescence size.*—Average of 10.4 cm in height and 14.8 cm in diameter.
- *Flower size.*—An average of 2.7 cm in depth and 3.1 cm in diameter, throat 3 mm in diameter, tube; 9 mm in length and 5 mm in diameter.
- *Lastingness of inflorescence.*—10 days, self-cleaning.
- *Flower aspect.*—Primarily upright to pedicel.
- *Peduncle.*—1 per rosette, very sturdy, oval in shape, held primarily upright 80° to soil level, surface is glabrous, slightly glaucous and moderately glossy, an average of 51.9 cm in length and 8 mm in width, color; a blend of 144A and 146B within waxy glaucous layer 193D.
- *Pedicels.*—Oval in shape, held in multiple angles, surface is glabrous, glossy, an average of 4.4 cm in length and 1.5 mm in width, 143A in color.
- *Flower buds.*—Oblanceolate in shape, surface matte and slightly velvety, an average of 2.4 cm in length and 8 mm in width, color; 94A, axially striped with a blend of N92B and 93A.
- *Tepals (perianth).*—6 (3 upper and 3 lower), rotate, oblanceolate in shape, fused base, entire margins, apex; lower acute, upper bluntly acute, both surfaces glabrous, slightly velvety and non-rugose with upper surface very slightly glossy and lower surface matt, thick substance, upper and lower tepals 2.8 cm in length, lower tepals 7 mm in width, upper tepal 9 mm in width, color (upper and lower tepals); when opening upper surface; 94A, darker longitudinal central stripe a blend of N92B and 93A, when opening lower surface; 94A, darker longitudinal central stripe 93A, fully open upper surface; 94B, darker longitudinal central stripe N92B, fading to 83B, stripe 83A, fully open lower surface; 94A, darker longitudinal central stripe 93A, fading to 83B, stripe 83A, base N92C, throat; NN155D, tube; N155A.
- *Bracts.*—Immature inflorescence bract; 1, dropped when individual flowers develop to open, broadly ovate in shape, 2.3 cm in length, 2.1 cm in width, color; upper surface N80B, base 157A, lower surface N186D, base 150C, pedicel bract; 1 at base of pedicel, 1 cm in length, 0.5 mm in width, color; 16C, apex 79A.

Reproductive organs:

*Gynoecium*.—Pistil; 1, average of 2.3 cm in length, stigma; club-shaped, 93B in color, style; 1.4 cm in length, color; 94C, distal end 93C, ovary; oblong in shape, 1 cm in length, 4 mm in width and 154A in color, pistillodes not present.

*Androecium*.—Stamens; 6 to 7, anthers; basifixed, oblong in shape, 5 mm in length, 1.5 mm in width, 153B in color, filament; 1.8 cm in length, color; 91C, distal end 93B, pollen; moderate in quantity and 191B in color, staminodes not present.

*Fruit/seed*.—None observed to date.

It is claimed:

1. A new and distinct cultivar of *Agapanthus* plant named 'A21001' as herein illustrated and described.

* * * * *